(12) United States Patent
Kubota et al.

(10) Patent No.: US 6,388,744 B1
(45) Date of Patent: May 14, 2002

(54) DISC-SHAPED RECORDING MEDIUM INSPECTION APPARATUS AND METHOD

(75) Inventors: Shigeo Kubota; Naoya Eguchi, both of Kanagawa; Yutaka Imai, Tokyo, all of (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/533,237

(22) Filed: Mar. 22, 2000

(30) Foreign Application Priority Data

Mar. 23, 1999 (JP) .......................................... 11-078192

(51) Int. Cl.[7] .............................................. G01N 21/00

(52) U.S. Cl. .................................................. 356/237.3

(58) Field of Search .............................. 356/237.3, 237, 356/338, 335–337, 339–343, 430, 431; 250/573, 571, 574, 221, 221.1, 559.06

(56) References Cited

U.S. PATENT DOCUMENTS

| 4,896,040 A | * | 1/1990 | Nakata et al. | 250/372 |
| 5,870,186 A | * | 2/1999 | Mogan et al. | 356/237 |
| 5,969,370 A | * | 10/1999 | Imaino et al. | 356/237.1 |

* cited by examiner

*Primary Examiner*—Frank G. Font
*Assistant Examiner*—Tu T. Nguyen
(74) *Attorney, Agent, or Firm*—Sonnenschein, Nath & Rosenthal (57) ABSTRACT

To inspect a disc-shaped recording medium accurately, promptly and nondestructively, a laser light emitted from a laser generator 4 is irradiated through an optical fiber 8, a rotatable diffusion plate 10 and an objective lens 13 to the surface of a disc 2. A solid-state image sensing device 15 detects a return component of the light, reflected from the surface of the disc 2. A processor 6 processes the output image from the solid-state image sensing device 15 to inspect the configuration of the signal recording surface of the disc 2.

20 Claims, 6 Drawing Sheets

DISC-SHAPED RECORDING MEDIUM INSPECTION APPARATUS AND METHOD

RELATED APPLICATION DATA

The present application claims priority to Japanese Application No. P11-078192 filed Mar. 23, 1999 which application is incorporated herein by reference to the extent permitted by law.

BACKGROUND OF THE INVENTION

1. Field of the Invention

The present invention relates to a disc-shaped recording medium inspection apparatus and method for inspecting the configuration of the signal recording surface of a disc-shaped recording medium.

2. Description of the Related Art

There has been proposed a disc-shaped recording medium having a signal recording layer to and/or which a signal is written and/or read by a recording/reproducing apparatus. As the disc-shaped recording media, there are already known a magnetic disc to which a magnetic field is applied by a magnetic head having a magnetic gap to write down a magnetic domain corresponding to a signal on a signal recording layer of the magnetic disc, and an optical disc to and/or from which a signal is written and/or read by irradiating thereto a laser light from an optical head of a recording/reproducing apparatus thereto. As the optical discs, there are available a read-only optical disc which has formed on a signal recording layer having a pit and land pattern corresponding to a signal, and a magneto-optical disc and phase-change type optical disc, capable of data write and read.

In the disc-shaped recording medium, a signal is normally written along a recording track formed on the signal recording layer. Specifically, in the above-described read-only optical disc, there are formed pits along the recording track.

For example, the interval between adjacent recording tracks (track pitch, hereinafter) of a conventional CD (Compact Disc) is 1600 nm, and its variation should not be more than 50 nm. On the other hand, the track pitch of a DVD (Digital Versatile Disc) adapted to the high recording density is 740 nm, and thus its variation should not be more than 23 nm or so. That is, as the track pitch is designed smaller in order to enable the high recording density, the configuration of the signal recording surface of the disc-shaped recording medium should be formed with a higher accuracy.

Accordingly, it is required that the inspection apparatus should be able to measure the surface configuration of a disc-shaped recording medium 10 nm or lower. Conventionally, a scanning tunneling microscope (STM) is used as such an inspection apparatus.

However, in case the STM is used to inspect the surface configuration of a disc-shaped recording medium, there is raised a problem that a sufficiently small part of the disc-shaped recording medium under inspection has to be taken by cutting as a sample for inspection by the STM, which however is a destructive inspection.

Also, the STM inspection takes much time. Accordingly, it has been difficult to measure a wide area of the disc-shaped recording medium. Furthermore, a long turnaround time is required, and it has been difficult to effectively feed back the inspection result to the recording process for production of a master disc for example.

OBJECT AND SUMMARY OF THE INVENTION

It is therefore an object of the present invention to overcome the above-mentioned drawbacks by providing a disc-shaped recording medium inspection apparatus and method, which can inspect the surface configuration of a disc-shaped recording medium accurately, promptly and nondestructively.

According to the present invention, there is provided an apparatus for inspecting the configuration of the signal recording surface of a disc-shaped recording medium. The inspection apparatus includes an imaging means and processing means. The imaging means emits a light having a wavelength falling within a predetermined range for irradiation to the signal recording surface, and detects a return component of the light, reflected from the signal recording surface. The processing means processes an output image from the imaging means. The inspection apparatus inspects the configuration of the signal recording surface based on a result of the output image processing by the processing means.

With the above inspection apparatus according to the present invention, it is possible to eliminate noise included in the output image effectively and promptly by processing the output image from the imaging means by the processing means. It is also possible to nondestructively detect a disc-shaped recording medium since the imaging means irradiates a light to the signal recording surface and detects a return light indicative of the configuration of the signal recording surface.

According to the present invention, there is also provided a method of inspecting the configuration of the signal recording surface of a disc-shaped recording medium. The inspection method includes an imaging step and a processing step. At the imaging step, a light having a wavelength falling within a predetermined range is irradiated to the signal recording surface and a return component of the light, reflected from the signal recording surface, is detected. At the processing step, an output image from the imaging step is processed. The configuration of the signal recording surface is inspected based on a result of the processing at the processing step.

With the above inspection method according to the present invention, it is possible to eliminate noise included in the output image effectively and promptly at the processing step by processing the output image from the imaging step. The inspection method can nondestructively detect a disc-shaped recording medium since a light is irradiated to the signal recording surface and a return light indicative of the configuration of the signal recording surface is detected at the imaging step.

As has been described above, the disc-shaped recording medium inspection apparatus according to the present invention can eliminate noise included in the output image from the imaging means effectively and promptly. Thus, the apparatus measure the configuration of the signal recording surface accurately based on the noise-eliminated output image. Also the inspection apparatus according to the present invention can nondestructively inspect a disc-shaped recording medium since the imaging means irradiates a light to the signal recording surface and detects a return light indicative of the configuration of the signal recording surface. Thus, the inspection apparatus according to the present invention can accurately inspect a disc-shaped recording medium in which the track pitch is small for a high recording density, and effectively feed back the inspection result to the manufacturing process for the disc-shaped recording medium with a reduced turnaround time.

Furthermore, the disc-shaped recording medium inspection method according to the present invention can eliminate noise included in the output image from the imaging step effectively and promptly. Thus, method measure the configuration of the signal recording surface accurately based on the noise-eliminated output image. Also the inspection method according to the present invention can nondestructively inspect a disc-shaped recording medium since a light is irradiated to the signal recording surface and a return light indicative of the configuration of the signal recording surface is detected at the imaging step. Thus, the inspection method according to the present invention can accurately inspect a disc-shaped recording medium in which the track pitch is small for a high recording density, and effectively feed back the inspection result to the manufacturing process for the disc-shaped recording medium with a reduced turnaround time.

These objects and other objects, features and advantages of the present intention will become more apparent from the following detailed description of the preferred embodiments of the present invention when taken in conjunction with the accompanying drawings.

DETAILED DESCRIPTION OF THE PREFERRED EMBODIMENTS

Figure 1:
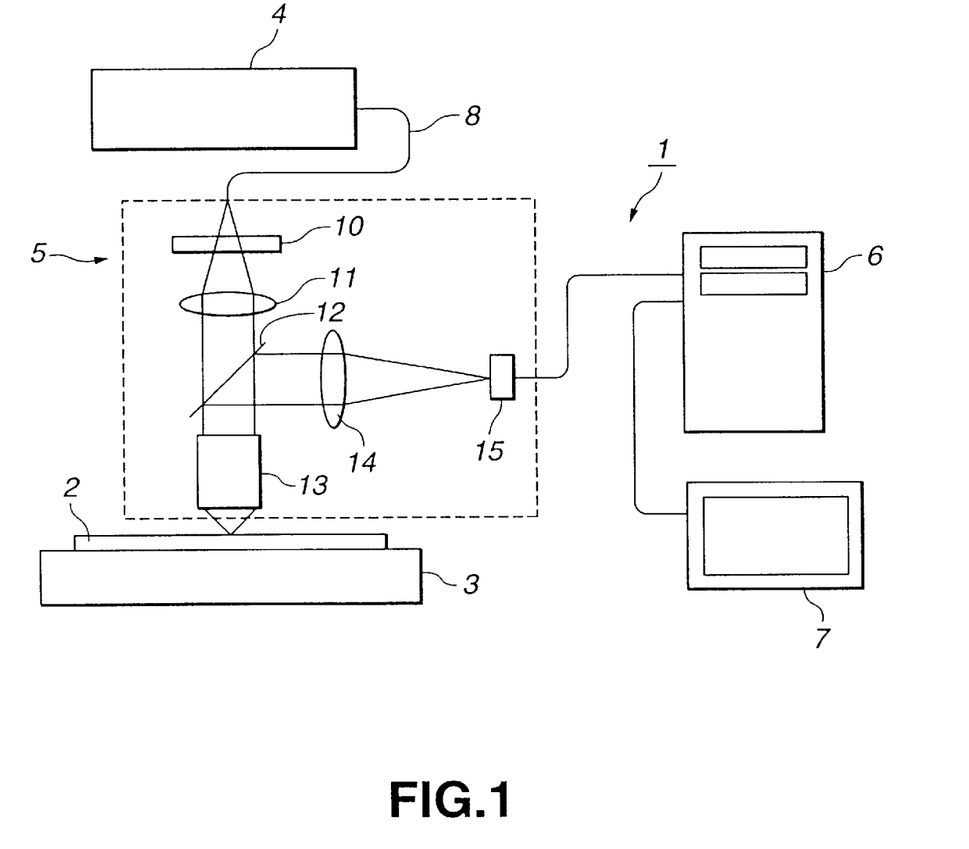
FIG. 1 shows a schematic view of an inspection apparatus according to the present invention.

Referring now to FIG. 1, there is illustrated a disc-shaped recording medium inspection apparatus according to the present invention. The apparatus is indicated generally with a reference 1.

The inspection apparatus 1 is an apparatus adapted for inspecting the configuration of the signal recording surface of a disc-shaped recording medium 2 (disc 2, hereinafter). The inspection apparatus 1 includes a sample stage 3 on which a disc 2 as a sample to be inspected is mounted, a laser generator 4, an imaging unit 5, a processor 6, and a display unit 7. The laser generator 4 and imaging unit 5 are optically connected to each other by an optical fiber 8. That is, in the inspection apparatus 1, a laser light emitted from the laser generator 4 is transmitted to the imaging unit 5 via the optical fiber 8.

The disc 2 may be a magneto-optical disc or a phase-change type optical disc having signal recording layers formed one on the other on a substrate, to which a signal can be written and/or read, or a read-only optical disc having a pit formed on a signal recording layer thereof Also, the disc 2 may be a magnetic recording medium such as a hard disc, or master discs used for manufacturing a variety of disc-shaped recording media.

The laser generator 4 may be large in size and weight in comparison with the imaging unit 5 and installed at any desired position since a laser light emitted from the laser generator 4 is transmitted to the imaging unit 5 via the optical fiber 8. The inspection apparatus 1 can reduce the spacial coherence of the laser light to reduce speckle noise since the laser light is transmitted through the optical fiber 8. The optical fiber 8 should desirably be made of a material such as synthetic quartz having a high transmittance for the far ultraviolet light, which makes it possible to minimize the loss of far ultraviolet laser light when it is transmitted.

In the inspection apparatus 1, the imaging unit 5 is installed movably radially of the disc 2 and the sample stage 3 is rotatable so that any point on the disc 2 can be irradiated with a laser light.

It is desired that the laser generator 4 is a far ultraviolet laser generator. Specifically, it may be, for example, a full solid-state neodymium YAG laser using its fourth harmonic to generate a laser light having a single wavelength of 266 nm in the single longitudinal and transverse mode, or the like. In the following explanation, the far ultraviolet light refers to an electromagnetic radiation having a wavelength of 200 to 300 nm.

In the inspection apparatus 1, the shorter the wavelength of a light irradiated to the disc 2, the higher the optical resolution is. However, if the wavelength is too short, the optical system becomes correspondingly difficult to design. Accordingly, the light for irradiation to the disc 2 should desirably have a far ultraviolet wavelength of 200 to 300 nm. The present invention is not limited to the above-mentioned neodymium YAG laser generator, but any other kinds of laser generators may be employed.

Furthermore, the laser generator 4 should desirably be a full solid-state laser, which will lead to an improved laser light generating efficiency as well as to a reduced size of the whole apparatus.

As shown in FIG. 1, the imaging unit 5 includes a rotatable diffusion plate 10, a collimator lens 11, a light splitter 12, an objective lens 13, a condenser lens 14 and a solid-state image sensing device 15. The rotatable diffusion plate 10, collimator lens 11, light splitter 12 and objective lens 13 are sequentially arranged along the optical path of a laser light.

The rotatable diffusion plate 10 has functions to reduce the spacial coherence of the laser light. In the inspection apparatus 1, if the laser light is irradiated directly to the disc 2, there is generated speckle noise in the output image from the solid-state image sensing device 15 since the laser light generally has a high coherence. For this reason, in the inspection apparatus 1, there is installed the rotatable diffusion plate 10 on the optical path of the laser light to suppress the speckle noise.

Similar to the optical fiber 8, the objective lens 13 should desirably be made of a material such as synthetic quartz having a high transmittance for the far ultraviolet light. Furthermore, it is desired that the objective lens 13 should have a numerical aperture NA of approximately 0.9. This will allow an improvement of the resolution of the laser light for irradiation to the disc 2.

The laser light converged onto the disc 2 by the objective lens 13 is reflected by the signal recording surface of the disc 2 to provide a return light which will go reversely along the incident optical path. The return light passes through the objective lens 13 and is incident upon the light splitter 12. The incident light is reflected by the light splitter 12 at a right angle and passes through the condenser lens 14, and then is incident upon the solid-state image sensing device 15. That is, the condenser lens 14 and the solid-state image sensing device 15 are arranged downstream of the light splitter 12 along the optical path of the return light.

The solid-state image sensing device 15 should desirably have a sufficient sensitivity and signal-to-noise ratio in the wavelength range of the laser light. Thus, the solid-state image sensing device 15 can produce an image with a high signal accuracy. Furthermore, it is desired that the solid-state image sensing device 15 should have many pixels. Specifically, the solid-state image sensing device 15 should have a million pixels or more. Having many pixels, the solid-state image sensing device 15 can cover a wide area of the signal recording surface of the disc 2 with a high signal accuracy. A charge coupled device (CCD) may be employed as the solid-state image sensing device 15. An image picked up by the solid-state image sensing device 15 is transmitted as a digital signal to the processor 6.

The processor 6 measures a track pitch, the configuration of a pit, etc. of the disc 2 by processing the output image from the solid-state image sensing device 15 in various manners. The processing by the processor 6 will be explained in further detail later. The processor 6 is composed of a microprocessor, memory, etc. The processing result of the processor 6 is displayed at the display unit 7. The processor 6 and the display unit 7 may be a computer or the like disposed together with, or separately from, other parts of the inspection apparatus 1, and connected to the imaging unit 5.

The inspection apparatus 1 will be explained in detail herebelow using specific numerical values by way of example. It should be noted however that the present invention is not limited to the examples but such numerical values may be determined for each disc 2 to be inspected.

On the assumption that in the above-mentioned inspection apparatus 1, the laser light has a wavelength $\lambda$ of 266 mn and the objective lens 13 has a numerical aperture of 0.9, the laser light can be converged to a spot having an airy radius (spot radius) of $0.6\lambda/NA=180$ (nm). Also, it is assumed that the objective lens 13 has an effective field of view of 100 $\mu$m in radius and the imaging system including the objective lens 13 has a magnification factor of 1000. Then, assume here that one of the million pixels of the solid-state image sensing device 15 has a size of 10 $\mu$m. This pixel size corresponds to 10 nm on the signal recording surface. The following description will be made based on the assumption that the spot radius of the laser light is 180 nm and the pixels of solid-state image sensing device 15 counts a million as in the above.

In a DVD capable of a high recording density, for example, the shortest recording mark formed on the recording track thereof is 400 nm and the track pitch is 740 nm. When inspecting this DVD with a laser light having the spot radius of 180 nm, the inspection apparatus 1 can determine the center of the recording track on the DVD and the edge configuration of the pits formed on the DVD with an accuracy of about 10 nm by processing the image output of the solid-state image sensing device 15 having the million pixels, which is an 8-bit digital image signal.

Figure 2:
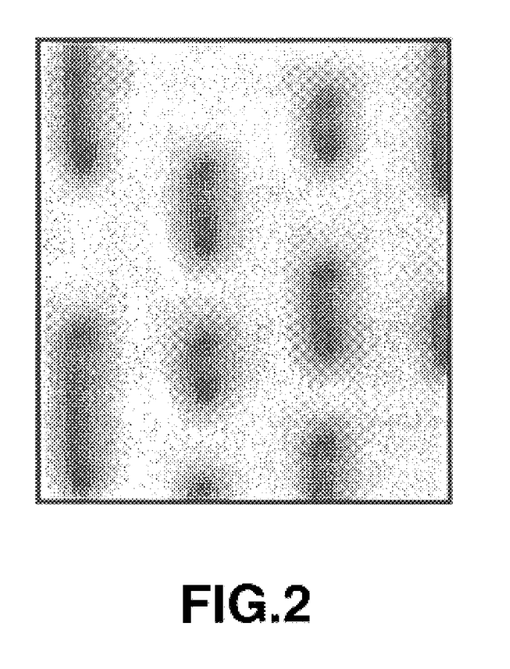
FIG. 2 shows an example of output image from the solid-state image sensing device of the inspection apparatus.

FIG. 2 shows one example of the output image of the solid-state image sensing device 15. However, FIG. 2 shows only 200×200 pixels being a part of the output image. That is, the output image from the solid-state image sensing device 15 shown in FIG. 2 covers an area of 2000 nm×2000 nm on the signal recording surface of the DVD. In FIG. 2, the pits on the signal recording surface of the DVD appear dark. In the DVD, each of the pits is formed as a physical change in configuration of the signal recording surface, and a string of the pits forms a recording track. In FIG. 2, the space between the adjacent recording tracks appears white and it is taken as a reference plane of the signal recording surface.

Figure 3:
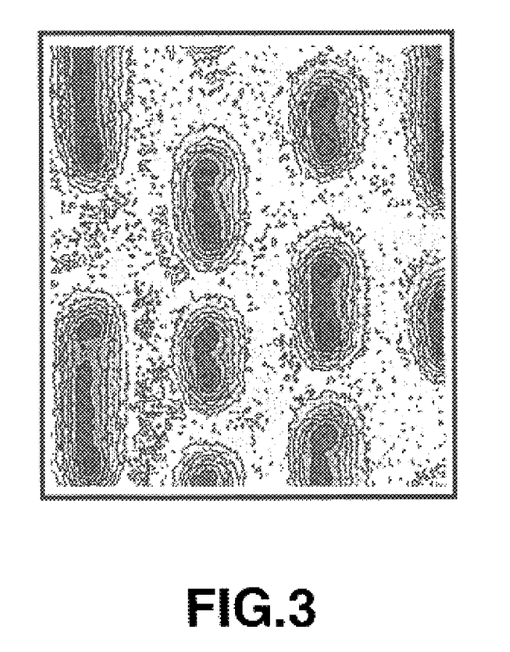
FIG. 3 shows an output image of pits edge-enhanced by processing the output picture.

The output image from the solid-state image sensing device 15 is edge-enhanced through an image processing by the processor 6. The result of the image processing is shown in FIG. 3. As will be seen from FIGS. 2 and 3, pits having the shortest recording mark of 400 nm in a DVD can be well distinguished. However, it is not apparent from FIGS. 2 and 3 whether or not the shape of these pits can be measured with an accuracy of about 10 nm. As will be seen, the pit edges shown in FIG. 3 are more definite than those in FIG. 2. However, it will also be evident from FIG. 3 that the pit shape measurement is dependent in performance upon the noise in the output image from the solid-state image sensing device 15.

Figure 4:
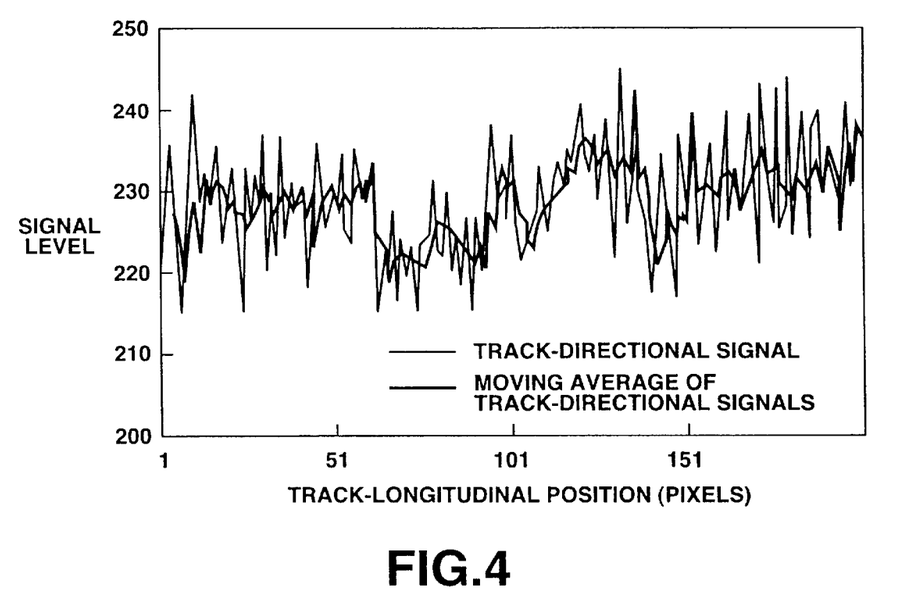
FIG. 4 shows a track-longitudinal signal obtained by measuring the signal levels of the output images in the reference plane of the signal recording surface in the recording track-longitudinal direction.

The signal level of the output image, shown in FIG. 2, at a position between the signal recording tracks, that is, in the reference plane of the signal recording surface, is measured to provide a track-longitudinal signal which is shown in FIG. 4. Also, a moving average of the track-longitudinal signals over five pixels is superposed on the track-longitudinal signal as shown in FIG. 4. Note that the track-longitudinal positions of 200 pixels are shown along the horizontal axis while the signal levels of the output image in FIG. 2 are shown along the vertical axis. Note that in FIG. 2, the output image is an 8-bit digital signal and the maximum signal level of the output image is 256. The results in FIG. 4 show that the mean signal level of the track-longitudinal signals is 229.25.

Figure 5:
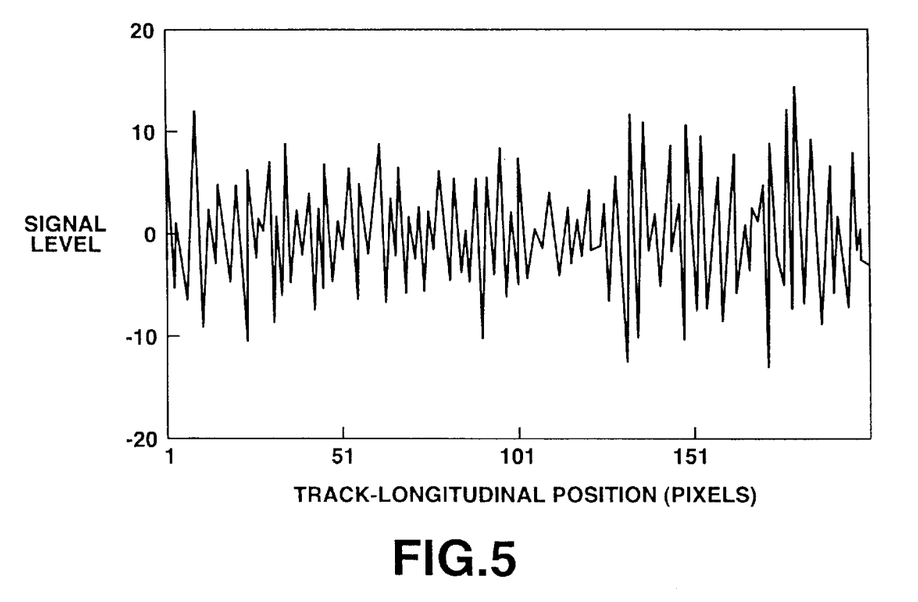
FIG. 5 shows a difference between the track-longitudinal signal of the output image and the moving average of the track-longitudinal signal.

FIG. 5 shows a difference between the track-direction signal and the moving average of the track-direction signals. That is, FIG. 5 shows an irregular noise in pixels of the track-direction signal. The noise is derived from the high frequency component of the output image. The vertical axis in FIG. 5 is calibrated ten times larger that in FIG. 4. It will be seen from FIG. 5 that the standard deviation of the signal is 6.4.

However, since the signal recording surface of the DVD is even with the reference plane, the curves in FIGS. 4 and 5 should ideally be flat. Thus, it is known from FIG. 4 and FIG. 5 that the output image from the solid-state image sensing device 15 suffers from a noise. This noise includes mainly an irregular noise contained in each pixel and a long-period noise having a duration over five pixels. As shown in FIG. 4 and FIG. 5, the standard deviation of the irregular noise is 5.0 and that of the long-period noise is 4.0.

The noise is considered to come from a noise caused by the solid-state image sensing device 15 itself and a speckle noise caused by the coherence of the laser light. It is considered that the element noise is caused by a shot noise, dark-current noise and a variable sensitivity of the solid-state image sensing device 15. The irregular noise in each pixel is considered to be an element noise while the long-term noise is to be a speckle noise.

In the inspection apparatus 1, when the laser light is irradiated to a disc sample through the rotatable diffusion plate 10, a speckle noise pattern moving at the rotational speed of the rotatable diffusion plate 10 is superimposed on a sample pattern detected by the solid-state image sensing device 15. Thus, the quantity of light detected by each of the pixels of the solid-state image sensing device 15 will vary for the speckle noise with the lapse of time. However, the speckle noise can be temporally averaged within the exposure time by increasing the rotational speed of the rotatable diffusion plate 10 sufficiently in comparison with the exposure time of the solid-state image sensing device 15. Hence, the rotatable diffusion plate 10 provided in the inspection apparatus 1 makes it possible to average the speckle noise temporally. Accordingly, it is considered that the speckle noise detected by the above-mentioned signal processing is a residual noise which has remained not sufficiently averaged, as shown in FIG. 4.

Since both of the irregular and long-period noises vary with the lapse of time, these noises can be reduced to $n^{-1/2}$ by imaging the same point of a sample n times by the solid-state image sensing device 15 and averaging the noises over the n output images. For example, by averaging the noises over 200 output images of the same point of the sample, each of the noises can be reduced to $200^{-1/2}$, that is to $1/14$. Therefore, the element noise having the standard deviation of 6.4 can be reduced to $1/14$, that is 0.45. Thus it becomes possible to reduce the noise influence to the quantum noise level 1 or less. On the other hand, other signal components than the noises included in the output image will not be reduced by the averaging because they have a regularity.

In an optical system such as the inspection apparatus 1 of the present invention in which the measuring performance is affected by the noise, not by the resolution of the objective lens 13, etc., if the noise is spatially irregular, the noise level can be lowered by statistically processing the noise with the regularity of the noise pattern taken in consideration.

Figure 6:
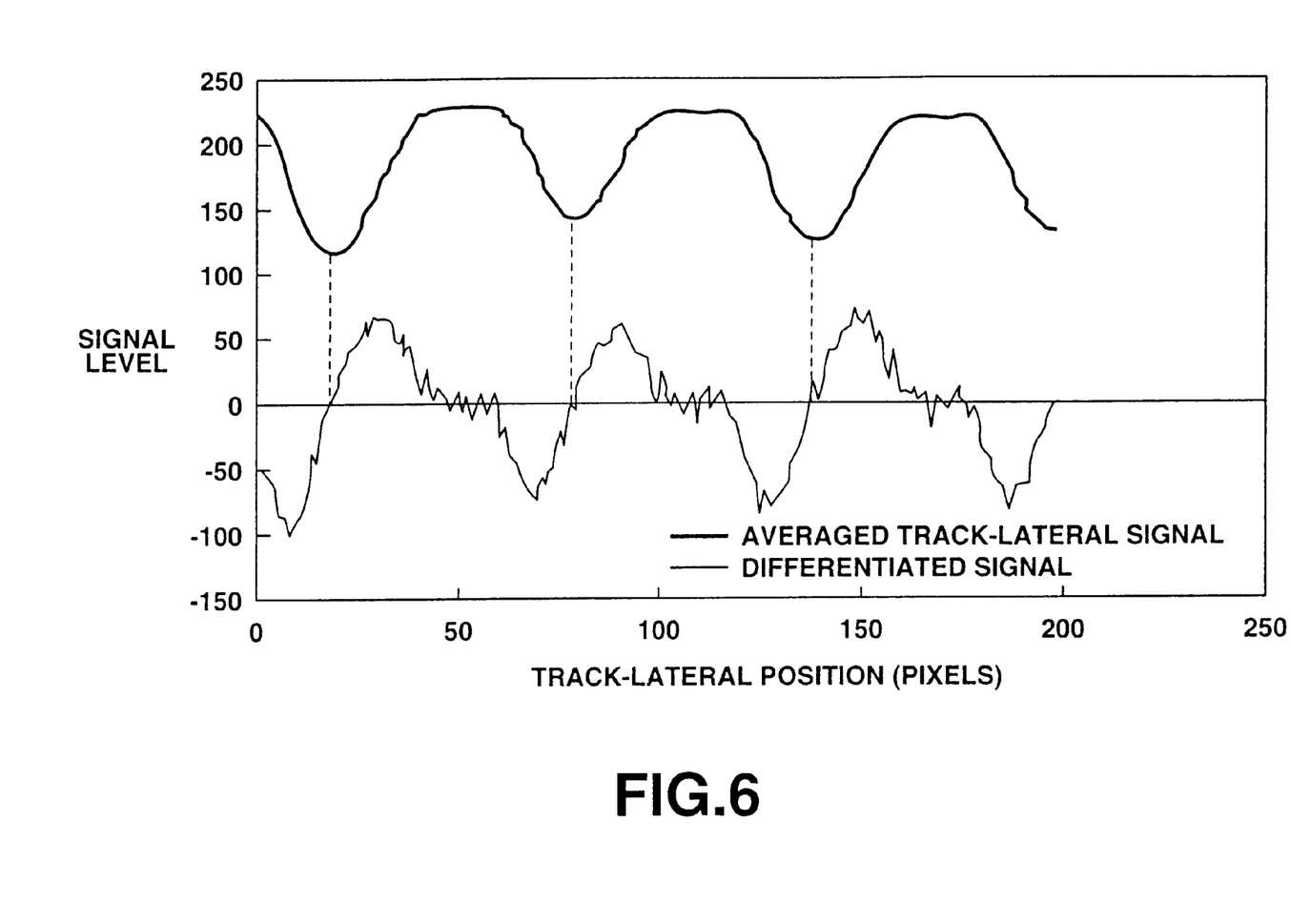
FIG. 6 shows an averaged track-lateral signal of the output image.

FIG. 6 shows an averaged track-lateral signal generated by integrating the signal levels of the output images in FIG. 2 longitudinally of the recording tracks and averaging the signal levels. The averaged track-lateral signal is numerically differentiated to provide a differentiated signal. This differentiated signal is also shown superposed on the averaged track-lateral signal in FIG. 6. More specifically, the averaged track-lateral signal in FIG. 6 represents a mean variation of the image signal in a direction crossing the recording tracks, and the differentiated signal represents a differentiated value of the averaged track-lateral signal. It will be apparent from FIG. 6 that in the process in which the output image from the solid-state image sensing device 15 is integrated in the direction crossing the recording tracks, the irregular noise is reduced by averaging and that the averaged track-lateral signal has a satisfactory signal-to-noise ratio.

The zero-cross points of the differentiated signal indicate peaks of the averaged track-lateral signal, respectively. Therefore, the inspection apparatus 1 can detect the peak positions of the recording tracks on the sample disc 2 by detecting the zero-cross points of the differentiated signal.

Thus, the inspection apparatus 1 can detect the peak positions of the averaged track-lateral signal based on the differentiated signal to detect nonuniformity of the track pitches.

Figure 7:
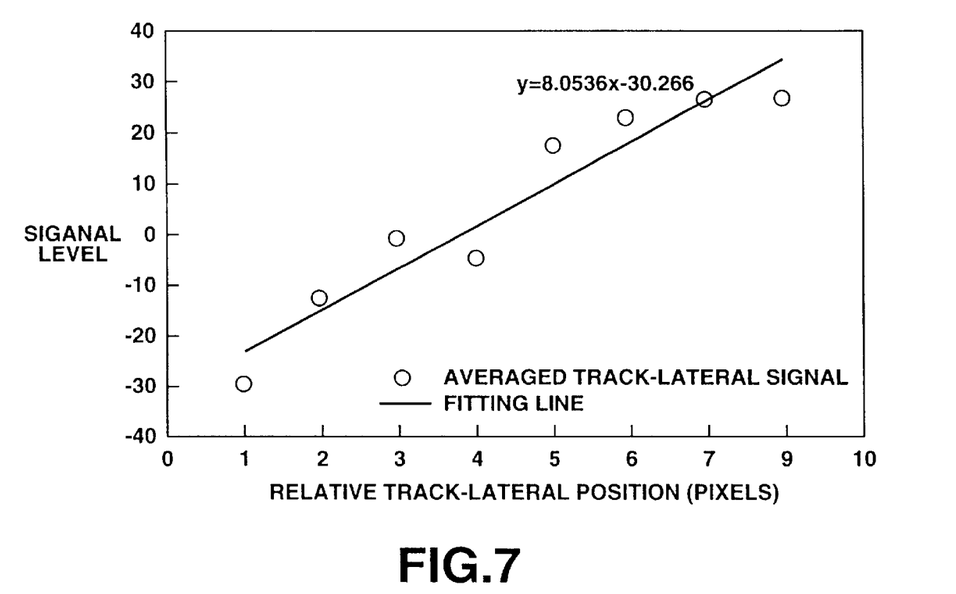
FIG. 7 shows signal levels near the zero-cross points of an averaged track-lateral signal of the output image.

More specifically, the averaged track-lateral signals for several pixels before and after the zero-cross point of the averaged tack-lateral signal should be fitted to a straight line and the zero-cross points be determined from a fitting line thus obtained, as shown in FIG. 7. To evaluate the influence of the residual noise in the averaged track-lateral signal near the zero-cross point, a standard deviation of the data as in FIG. 7 from the obtained straight line was calculated. The standard deviation was 5.7. The actual standard deviation is 0.57 since the signal level of the averaged track-lateral signal is shown enlarged 10 times in FIG. 7. This value approximately corresponds to the expected value of 0.45 of the irregular noise.

Next, the influence of the standard deviation on the accuracy of detection of the zero-cross point is verified. Division of the standard deviation of 5.7 by an average gradient of 8.054/pixel of the differentiated signal results in 0.709 pixel. Since one pixel corresponds to 10 nm on the sample disc 2, it will be known that the track pitches can be measured with accuracy of 10 nm or less.

Concerning three recording tracks shown in FIG. 2, the center positions of the recording tracks, mean average gradient of the differentiated signals in the vicinity of the center positions and a standard deviation from the fitting line were determined. The results are shown in Table 1.

TABLE 1

| Center position of recording track (in pixels) | Mean gradient of differentiated signals (in 10 × signal level/pixel) | Standard deviation from fitting line (in 10 × signal level) | Track pitch (in pixels) | Estimated measurement error (in pixels) | Estimated measurement error of track pitch (in %) |
| --- | --- | --- | --- | --- | --- |
| 18.866 | 8.792 | 7.683 | 60.892 | 0.874 | 1.5 |
| 79.758 | 8.054 | 5.710 | 59.679 | 0.709 | 1.2 |
| 139.438 | 8.050 | 4.852 |  | 0.603 | 1.0 |

It will be seen from Table 1 that the track pitches between the two adjacent recording tracks are 60.892 pixels and 59.679 pixels respectively. There is an error of about 2% between the track pitches. On the other hand, since the estimated measurement error is 1% to 1.5%, the error of about 2% between the track pitches is significant. Note that the track pitch allowance specified in the standard for the CDs (Compact Disc) being a disc-shaped recording medium is 3%.

The accuracy with which the center positions of the recording tracks are detected also depends on the rate of change of the detected averaged track-lateral signal. The rate of change is influenced by the contrast of the averaged track-lateral signal. Thus, when detecting the edge positions of pits based on the averaged track-lateral signal, the influence of the noise can be eliminated only by a relatively simple averaging method since the rate of change of the averaged track-lateral signal near edges of the pits is larger than that at the peak positions of the recording tracks.

Figure 8:
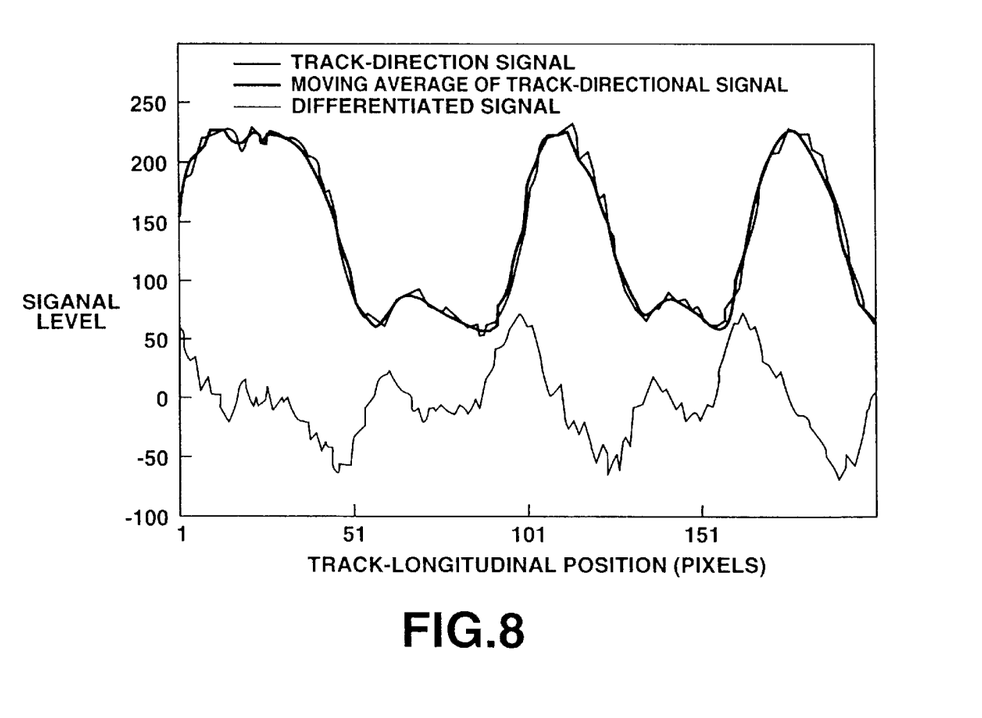
FIG. 8 shows a track-longitudinal signal obtained by measuring the signal levels of the output image at the center positions of the recording tracks in the recording track-longitudinal direction.

The signal level of the output image (in FIG. 2) at the center positions of the recording tracks, determined as in FIGS. 6 and 7, was measured longitudinally of the recording tracks to provide a track-longitudinal signal. The track-longitudinal signal is shown in FIG. 8. In FIG. 8, a moving average of the track-longitudinal signals over 5 pixels is superposed on the track-longitudinal signal itself and also a differentiated signal generated by numerically differentiating the track-directional signal, is superposed on the track-longitudinal signal, as in FIG. 4.

The inspection apparatus 1 can detect the edge positions of the pits by detecting the zero-cross points of the differentiated signal based on the track-longitudinal signal at the center positions of the recording tracks, as in the detection of the center positions of the recording tracks shown in FIG. 7.

FIG. 8 shows that the standard deviation of the track-longitudinal signal from the displacement average is 3.5. This value is slightly smaller than the standard deviation of 5.0 of the irregular noise of the track-direction signal in the reference plane. On the other hand, the variation in signal level of the track-longitudinal signal along the direction of the recording tracks is a maximum of 16 per pixel. Therefore, division of the standard deviation of 3.5 indicative of the irregular noise of the track-longitudinal signal by the maximum variation in signal level of 16 results in 0.23 pixel. This means that the error in detection of the edge positions of the pits is approximately ⅓ of the error in detection of the center positions of the above-mentioned recording tracks. That is, the inspection apparatus 1 can detect the edge positions of the pits with an accuracy of 5 nm or less.

As in the detection of the edge positions of the pits, the inspection apparatus 1 can detect the width of the pits from the output image shown in FIG. 2 by generating a track-lateral signal measured in a direction crossing the recording tracks and detecting the zero-cross points of the differentiated signal of this track-lateral signal.

Figure 9:
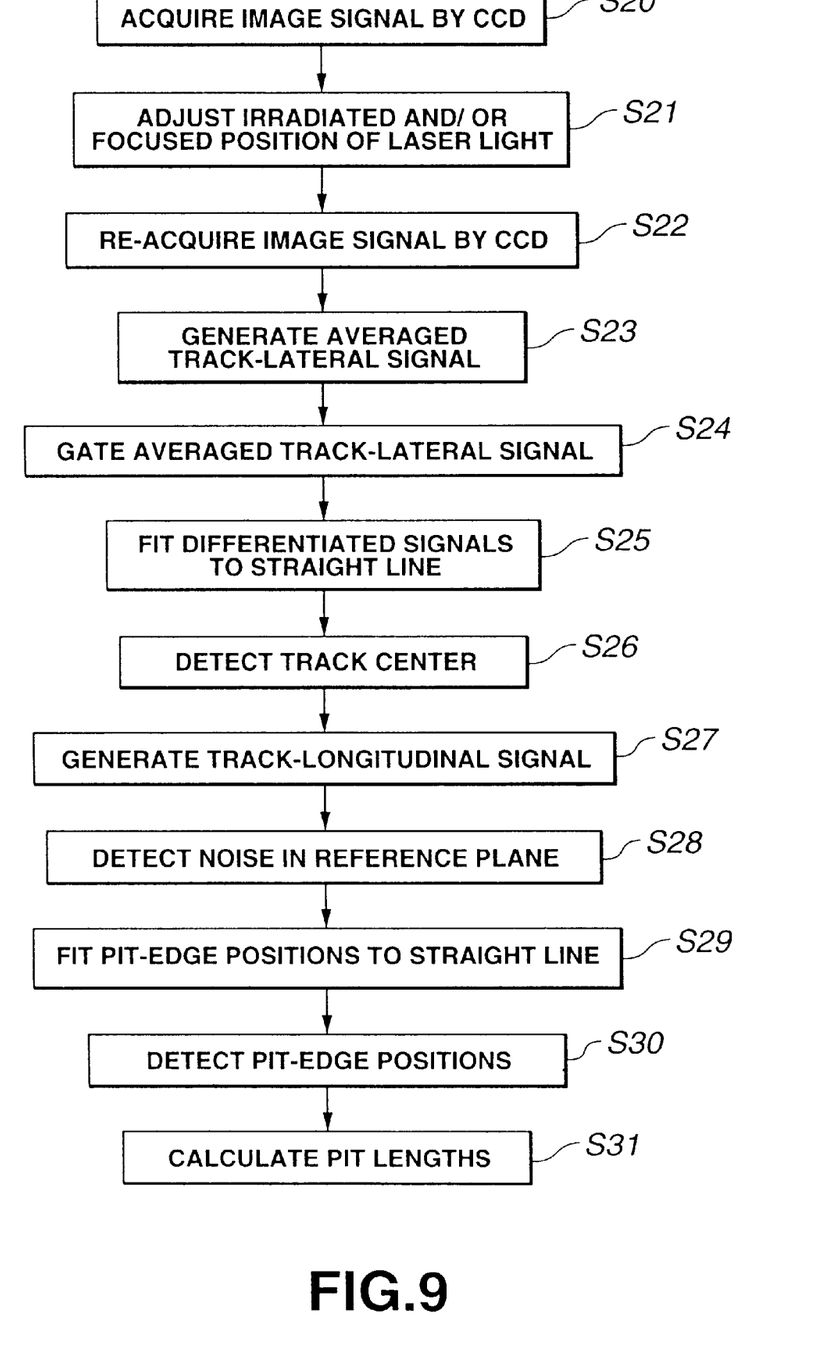
FIG. 9 is flow chart of operations in processing of the inspection apparatus.

The inspection apparatus 1 constructed as in the foregoing functions as will be described below with reference to FIG. 9.

First, the sample disc 2 to be inspected is placed on the sample stage 3, and a laser light emitted from the laser generator 4 is irradiated by the imaging unit 5 to the surface of the disc 2. The solid-state image sensing device 15 included in the imaging unit 5 then detects a return component of the laser light reflected from the surface of the disc 2, and the output image from the solid-state image sensing device 15 is supplied to the processor 6.

At step S20, the processor 6 thus receives the output image from the imaging unit 5.

At step S21, the processor 6 analyzes the received output image, and directs the imaging unit 5 to adjust the irradiated point, focused point, etc. of the laser light for an appropriate focusing of the output image, while rotating the sample stage 3. Then the imaging unit 5 picks up an image of a desired point on the disc 2 again with a appropriate focusing. Thus, the processor 6 can accurately detect the center positions of the recording tracks and configuration of the pits based on the proper output image.

At step S22, the processor 6 receives the properly focused output image from the imaging unit 5 again.

At step S23, the processor 6 integrates and averages the signal levels of the output images longitudinally the recording tracks to generate an averaged track-lateral signal.

At step S24, the processor 6 gates the averaged track-lateral signal, and extracts the zero-cross points of the differentiated signal generated by numerically differentiating the averaged track-lateral signal. Thus, it is possible to prevent any erroneous processing with the zero-cross points independent of the peak positions at a subsequent step.

At step S25, the differentiated signal is fitted to a straight line at positions near the zero-cross points extracted at step S24.

At step S26, the zero-cross points are detected based on the straight line to which the differentiated signals are fitted at step S25, to detect the center positions of the recording tracks.

At step S27, track-longitudinal signals are generated by measuring the signal levels of the output image at the center positions of the recording tracks detected at step S26 longitudinally of the recording tracks, and a moving average of the track-direction signals is calculated.

At step S28, track-longitudinal signals are generated in the reference plane of the signal recording surface of the disc 2, and a moving average of the track-direction signals is calculated to detect a noise at a position in the reference plane. Also, from the track-longitudinal direction signals at the center positions of the recording tracks, generated at step S27, there is removed a noise based on the noise amount detected at the position in the reference plane.

At step S29, the differentiated signals are fitted to a straight line at positions near the zero-cross points thereof generated by numerically differentiating the track-longitudinal signals generated at step S27.

At step S30, edge positions of the pits are detected based on the straight line to which the differentiated signals are fitted at step S29.

Finally at step S31, a distance between the edge positions detected at S30 is determined and the lengths of the pits are calculated.

As has been described above, there takes place in the inspection apparatus 1 a noise in each pixel, which is considered to be caused by an element noise in the output image from the solid-state image sensing device 15. The standard deviation of the noise is about 5.0 in the reference plane and 3.5 in the recording tracks of the signal recording surface. The large noise in the reference plane is considered to be caused by a surface irregularity in the reference plane of the sample disc 2 to be inspected.

Also the noise included in the output image from the solid-state image sensing device 15 and two or three times larger than the standard deviation of the element noise is considered to be caused by the speckle noise or a noise caused by point defects on the disc 2.

With the inspection apparatus 1, it is possible to sufficiently reduce the element noise and speckle noise by a combination of an increase in rotational speed of the rotatable diffusion plate 10, increase in exposure time of the solid-state image sensing device 15, averaging of many output images from the solid-state image sensing device 15, etc. Thus the inspection apparatus 1 can detect defects on the sample disc 2 with a high ability of distinction.

Also, the inspection apparatus 1 can easily measure width of the pits and gradients of side walls as well as the edge positions and lengths of the pits.

Furthermore, the inspection apparatus 1 can inspect the disc 2 which are master discs for manufacturing a variety of disc-shaped recording media such as an optical disc having pits and magnetic recording media such as a hard disc etc. since it can measure the configuration of the signal recording surface by emitting a laser light for irradiation to the sample disc 2 to be inspected.

While the present invention has been described with reference to specific embodiments chosen for purpose of illustration. It should be apparent that numerous modifications could be made thereto by those skilled in the art without departing from the basic concept and scope of the present invention.

What is claimed is:

1. A disc-shaped recording medium inspection apparatus for inspecting a configuration of a signal recording surface of a disc-shaped recording medium, the apparatus comprising:

an imaging means for emitting a light having a wavelength falling within a predetermined range to irradiate the signal recording surface, for detecting a return component of the light as reflected from the signal recording surface, and for outputting an output image, wherein the predetermined range of the light wavelength is 200 nm to 300 nm;

means for processing the output image from the imaging means to form a result; and means for inspecting the configuration of the signal recording surface based on the result of the output image processing by the means for processing.

2. The apparatus as set forth in claim 1, wherein the imaging means is configured to emit a light having a wavelength within a far ultraviolet wavelength range.

3. The apparatus as set forth in claim 2, wherein the imaging means is configured to detect the return component of the light by a solid-state image sensing device, wherein the solid-state image sensing device is configured to detect the light having a wavelength within the far ultraviolet wavelength range.

4. The apparatus as set forth in claim 2, wherein the imaging means comprises a synthetic quartz-made objective lens to converge the light onto the signal recording surface.

5. The apparatus as set forth in claim 1, wherein the imaging means is configured to adjust an irradiated and/or focused position of the light as a function of the result of the output image processing by the means for processing.

6. The apparatus as set forth in claim 1, wherein the imaging means further comprises means for reducing spacial coherence of the light.

7. The apparatus as set forth in claim 6, wherein the means for reducing is an optical fiber.

8. The apparatus as set forth in claim 6, wherein the means for reducing is a rotatable diffusion plate.

9. The apparatus as set forth in claim 1, wherein the means for processing is configured to average the output image from the imaging means in a recording track-longitudinal direction to generate an averaged track-lateral signal indicative of a variation of averaged signal levels in a recording track-lateral direction, numerically differentiate the averaged track-lateral signal to generate a differentiated signal, and detect recording track centers on the signal recording surface based on zero-cross points of the differentiated signal.

10. The apparatus as set forth in claim 1, wherein the means for processing is configured to generate a track-longitudinal signal indicative of a variation of a signal level in a recording track-longitudinal direction based on the output image from the imaging means, numerically differentiate the track-longitudinal signal to generate a differentiated signal, and detect pit edge positions on a recording track based on zero-cross points of the differentiated signal.

11. The apparatus as set forth in claim 1, wherein the means for processing is configured to generate a track-lateral signal indicative of a variation of a signal level in a recording track-lateral direction based on the output image from the imaging means, numerically differentiate the track-lateral signal to generate a differentiated signal, and detect a pit width on a recording track based on zero-cross points of the differentiated signal.

12. The apparatus as set forth in claim 1, wherein the wavelength is defined by $\lambda$ and wherein the imaging means comprises an objective lens that defines a numerical aperture NA such that a spot radius of 180 (nm) is defined by the equation $0.61\lambda/NA=180$ (nm).

13. A method of inspecting a configuration of a signal recording surface of a disc-shaped recording medium, the method comprising the steps of:

emitting a light having a wavelength falling within a predetermined range to irradiate the signal recording surface, wherein the predetermined range of the light wavelength is 200 nm to 300 nm;

detecting a return component of the light as reflected from the signal recording surface to form an image;

outputting the image as an output image;

processing the output image to form a result; and inspecting the configuration of the signal recording surface as a function of the result of the processing obtained at the processing step.

14. The method as set forth in claim 13, wherein the wavelenght is defined by $\lambda$ and wherein the imaging means comprises an objective lens that defines a numerical aperture NA such that a spot radius of 180 (nm) is defined by the equation $0.61\lambda/NA=180$ (nm).

15. The method as set forth in claim 13, further comprising:

adjusting an irradiated position and/or focused position of the light as a function of the result of the processing obtained at the processing step.

16. The method as set forth in claim 13, wherein, at the processing step, averaging the output image obtained at the imaging step in a recording track direction to generate an averaged track-lateral signal indicative of a variation of averaged signal level in a recording track-lateral direction, numerically differentiating the averaged track-lateral signal to generate a differentiated signal, and detecting recording track center positions on the signal recording surface based on zero-cross points of the differentiated signal.

17. The method as set forth in claim 13, wherein, at the processing step, generating a track-longitudinal signal indicative of a variation of a signal level in a recording track direction based on the output image obtained at the outputting step, numerically differentiating the track-longitudinal signal to generate a differentiated signal, and detecting pit edge positions on a recording track based on zero-cross points of the differentiated signal.

18. The method as set forth in claim 13, wherein, at the processing step, generating a track-lateral signal indicative of a variation of a signal level in a recording track-lateral direction based on the output image obtained at the imaging step, numerically differentiating the track-lateral signal to generate a differentiated signal, and detecting pit widths on a recording track based on zero-cross points of the differentiated signal.

19. The method as set forth in claim 13, wherein emitting a light includes emitting a light having a wavelength within a far ultraviolet wavelength range.

20. The method as set forth in claim 19, wherein detecting a return component of the light includes employing a solid-state image sensing device configured to detect light having a wavelength within the far ultraviolet wavelength range.

* * * * *